United States Patent [19]

Blank et al.

[11] 4,338,261

[45] Jul. 6, 1982

[54] PROCESS FOR THE PREPARATION OF 1-NAPHTHYLAMINE-4,6-DISULPHONIC ACID AND 1-NAPHTHYLAMINE-2,4,6-TRISULPHONIC ACID

[75] Inventors: Heinz U. Blank, Odenthal; Horst Behre, Odenthal-Eikamp; Hans W. Linden, Leverkusen; Werner Mentzel, Cologne, all of Fed. Rep. of Germany

[73] Assignee: Bayer Aktiengesellschaft, Leverkusen, Fed. Rep. of Germany

[21] Appl. No.: 247,416

[22] Filed: Mar. 25, 1981

[30] Foreign Application Priority Data

Apr. 5, 1980 [DE] Fed. Rep. of Germany ....... 3013275

[51] Int. Cl.$^3$ ............................................ C07C 143/60
[52] U.S. Cl. .................................................. 260/508
[58] Field of Search ....................................... 260/508

[56] References Cited

FOREIGN PATENT DOCUMENTS 4021 11/1891 Fed. Rep. of Germany .
1490508 6/1967 France .
15223 of 1894 United Kingdom .
161859 of 1921 United Kingdom ................ 260/508

OTHER PUBLICATIONS

Beilstein, vol. XIV, p. 790, 1943.
Ullmann, Enzyklopädie der Tech. Chem., vol. 12, p. 628 (1960).

Primary Examiner—Nicky Chan
Attorney, Agent, or Firm—Sprung, Horn, Kramer & Woods

[57] ABSTRACT

Improved process for the preparation of 1-naphthylamine-4,6-disulphonic acid wherein the sulphonation of the 1-naphthylamine-6-sulphonic acid is carried out by adding the oleum at a temperature of 10° to 70° C., either to initially introduce sulphuric acid simultaneously with the 1-naphthylamine-6-sulphonic acid or to 1-naphthylamine-6-sulphonic acid, which is dissolved or suspended in sulphuric acid, and by using such a molar ratio of sulphur trioxide to 1-naphthylamine-6-sulphonic acid that 1.2 to 3 mols of sulphur trioxide are present per mol of 1-naphthylamine-6-sulphonic acid. The sulphonation mixture formed in the preparation can be sulphonated in a second sulphonation stage to 1-naphthylamine-2,4,6-trisulphonic acid.

6 Claims, No Drawings

PROCESS FOR THE PREPARATION OF 1-NAPHTHYLAMINE-4,6-DISULPHONIC ACID AND 1-NAPHTHYLAMINE-2,4,6-TRISULPHONIC ACID

The invention relates to a new process for the preparation of 1-naphthylamine-4,6-disulphonic acid and 1-naphthylamine-2,4,6-trisulphonic acid.

1-Naphthylamine-4,6-disulphonic acid and 1-naphthylamine-2,4,6-trisulphonic acid are important intermediate products for the preparation of dyestuffs.

Various processes for the preparation of 1-naphthylamine-4,6-disulphonic acid are already known. Thus, for example, a process for the preparation of 1-naphthylamine-4,6-disulphonic acid, according to which 1-naphthylamine-6-sulphonic acid is sulphonated with manganese dioxide and sodium bisulphite, is described in French Patent Specification No. 1,490,508. However, this process has the disadvantage that manganese dioxide, which is expensive, is used, a poor space/time yield is achieved and large amounts of mother liquor containing salts are obtained.

This process thus cannot be used for the preparation of 1-naphthylamine-4,6-disulphonic acid on an industrial scale.

The processes for the preparation of 1-naphthylamine-4,6-disulphonic acid in which sulphonation of 1-naphthylamine-6-sulphonic acid is carried out with oleum are of interest in industry. Such processes are described, for example, in Beilstein H, XIV, page 790; Ullmann, Enzyklopädie der Technischen Chemie (Encyclopaedia of Industrial Chemistry), Volume 12, page 628 (1960); German Patent Application C 4021 (1891), reported in Freiedländer 33, page 432; and British Patent Specification No. 15,223.

According to the statements in Beilstein, 1-naphthylamine-4,6-disulphonic acid is said to be formed by heating 1-naphthylamine to 120° C. with excess 25% strength oleum, or by the action of 25% strength oleum on 1-naphthylamine-4-sulphonic acid at temperatures below 30° C. for several days. According to Ullmann, 1-naphthylamine-4,6-disulphonic acid is obtained by introducing 1-naphthylamine-4-sulphonic acid into 25% strength oleum and subsequently stirring the mixture at 30° C. for 25 hours. According to German Patent Application No. C 4021 which is reported in Friedländer, 1-naphthylamine-4,6-disulphonic acid is obtained by treating 1-naphthylamine-6-sulphonic acid with approximately 10% strength oleum at 100°-150° C. These processes have the disadvantage, however, that mixtures which consist, for example, of 1-naphthylamine-4,6- and -4,7-disulphonic acid and which are difficult to separate are formed therein.

According to the process described in British Patent Specification No. 15,223, 1-naphthylamine-6-sulphonic acid is sulphonated by being introduced into 25% strength oleum and subsequently warming the sulphonation mixture to 50° to 60° C. for 3 to 4 hours. However, 1-naphthylamine-4,6-disulphonic acid is not isolated; rather, the sulphonation mixture is immediately sulphonated further to give 1-naphthylamine-2,4,6-trisulphonic acid. Repetition of this sulphonation process showed that considerable amounts of undesired 1-naphthylamine-3,6-disulphonic acid and 1-naphthylamine-2,4,6-trisulphonic acid are formed. Because of the poor yields of the desired 1-naphthylamine-4,6-disulphonic acid and of the difficulties in separating the isomers, this process is of no significance for an industrial production.

It has now been found that a process for the preparation of 1-naphthylamine-4,6-disulphonic acid which can also be carried out on an industrial scale is achieved when the sulphonation of 1-naphthylamine-6-sulphonic acid is carried out under certain conditions. The certain conditions consist in (a) adding the sulphonation agent oleum to 1-naphthylamine-6-sulphonic acid, which is dissolved or suspended in sulphuric acid, or simultaneously adding the sulphonation agent oleum and 1-naphthylamine-6-sulphonic acid to initially introduced sulphuric acid, and (b) using a molar ratio of sulphur trioxide: 1-naphthylamine-6-sulphonic acid such that 1.2 to 3 mols of sulphur trioxide are present per mol of 1-naphthylamine-6-sulphonic acid. An increase in the yields of 1-naphthylamine-4,6-disulphonic acid of about 20%, compared with the yield obtained by the most favourable process according to the state of the art, is achieved by the combination, according to the invention, of these two particular measures. Furthermore, the 1-naphthylamine-4,6-disulphonic acid still only contains negligible traces of undesired 1-naphthylamine-3,6-disulphonic acid.

The invention thus relates to a process for the preparation of 1-naphthylamine-4,6-disulphonic acid by sulphonating 1-naphthylamine-6-sulphonic acid with oleum, working up the sulphonation mixture by introducing it into water, and isolating the 1-naphthylamine-4,6-disulphonic acid, which is characterised in that the oleum is added at a temperature of 10° to 70° C., preferably 20° to 40° C., either simultaneously with the 1-naphthylamine-6-sulphonic acid to initially introduced sulphuric acid or, preferably, to 1-naphthylamine-6-sulphonic, which is dissolved or suspended in sulphuric acid, and that such a molar ratio of sulphur trioxide: 1-naphthylamine-6-sulphonic acid is used that 1.2 to 3 mols of sulphur trioxide are present per mol of 1-naphthylamine-6-sulphonic acid.

The oleum is advantageously added at temperatures from 10° to 70° C., preferably at temperatures from 20° to 40° C.

The oleum to be used in the process according to the invention can contain 20 to 100% by weight of sulphur trioxide. Oleum which contains 50 to 80 percent by weight of free sulphur trioxide is preferably used.

80 to 100% strength, in particular 96 to 100% strength, sulphuric acid is preferably used for dissolving or suspending the 1-naphthylamine-6-sulphonic acid. The amount of sulphuric acid used for obtaining the solution or suspension is advantageously chosen such that 6 to 8 mols of sulphuric acid are present per mol of 1-naphthylamine-6-sulphonic acid.

If water-containing sulphuric acid is used for obtaining the solution or suspension, or 1-naphthylamine-6-sulphonic acid which is not dry but moist is employed, sulphur trioxide (in the form of oleum) is to be added in such an amount, in excess of the amount of 1.2 to 3 mols of sulphur trioxide per mol of 1-naphthylamine-6-sulphonic acid, as is necessary for the water contained in the reagents to be bonded as sulphuric acid.

When the oleum has been added, the reaction mixture is allowed to react completely at temperatures from 20° to 40° C., preferably 25° to 35° C., whilst stirring. The time for complete reaction is between 3 and 30 hours, preferably 8 to 24 hours.

The 1-naphthylamine-4,6-disulphonic acid is obtained from the finished sulphonation mixture in a manner which is in itself known, by introducing the mixture into water and filtering off the acid which has crystallised out, or filtering off the acid monosodium salt after salting out, for example with sodium chloride.

In the case of further processing of the 1-naphthylamine-4,6-disulphonic acid to 1-naphthylamine-2,4,6-trisulphonic acid, it is not necessary to isolate the 1-naphthylamine-4,6-disulphonic acid. Rather, in a second sulphonation stage, oleum is added to the finished sulphonation mixture at temperatures of 70° to 120° C., preferably 80° to 100° C., in an amount such that 1 to 2.5 mols, preferably 1.5 to 2 mols, of sulphur trioxide are present per mol of 1-naphthylamine-6-sulphonic acid originally employed. When the oleum has been added, the sulphonation mixture is allowed to react completely at 70° to 120° C., preferably 80° to 100° C., for 2 to 8 hours. The 1-naphthylamine-2,4,6-trisulphonic acid formed is isolated in a manner which is in itself known, by introducing the sulphonation mixture into water. The sulphonic acid is obtained as the free acid, or as the acid disodium salt, by salting out, for example with sodium chloride.

As a result of its considerably higher content of 1-naphthylamine-4,6-disulphonic acid and its low content of 1-naphthylamine-3,6-disulphonic acid, the sulphonation mixture obtained in the preparation, according to the invention, of 1-naphthylamine-4,6-disulphonic acid gives 1-naphthylamine-2,4,6-trisulphonic acid in considerably higher yields and higher purity than the sulphonation mixtures containing 1-naphthylamine-4,6-disulphonic acid which are obtainable according to the state of the art.

solution has formed. 246 g of oleum (65% strength) (=2 mols of $SO_3$) are then added dropwise at 30° C. in the course of 30 minutes. The sulphonation mixture is subsequently stirred at 30° C. for 16 hours.

The sulphonation mixture is then introduced into 1,434 g of water, whilst stirring at a rate such that the temperature of the aqueous mixture formed rises to 90° to 95° C. After a few minutes, the 1-naphthylamine-4,6-disulphonic acid precipitates. The mixture is allowed to cool to 20° C., whilst stirring (cooling time: 5 to 6 hours), and the precipitate is filtered off. The filter cake is pressed off thoroughly.

The yield of 1-naphthylamine-4,6-disulphonic acid is 321 g (=80.6% of theory, relative to the 1-naphthylamine-6-sulphonic acid employed).

High pressure liquid chromatography of the product filtered off showed the following composition: 1-naphthylamine-4,6-disulphonic acid: 76.1% by weight; 1-naphthylamine-3,6-disulphonic acid: 0.1% by weight; 1-naphthylamine-2,4,6-trisulphonic acid: trace; remainder to make up to 100%: water/sulphuric acid.

EXAMPLES 2 TO 5

The procedure followed is as described in Example 1, but other molar ratios of sulphur trioxide: 1-naphthylamine-6-sulphonic acid and other reaction temperatures and subsequent stirring times are used.

The results obtained in these preparation processes are summarized in the following table. The composition of the 1-naphthylamine-4,6-disulphonic acid isolated was determined by means of high pressure liquid chromatography.

TABLE

| Example No. | Sulphonation conditions | | | Amount weighed (g) | Solid isolated Composition (% by weight)* | | | | Yield of 1-$NH_2$-4,6 (mol %) |
|---|---|---|---|---|---|---|---|---|---|
| | Molar ratio of $SO_3$: 1-$NH_2$-6-S | Reaction temperature (°C.) | Subsequent stirring time (hours) | | 1-$NH_2$-6 | 1-$NH_2$-3,6 | 1-$NH_2$-4,6 | 1-$NH_2$-2,4,6 | |
| 2 | 2.5:1 | 30 | 9 | 351 | trace | 2.8 | 68.5 | trace | 79.2 |
| 3 | 2:1 | 40 | 8 | 308 | trace | 0.6 | 76.7 | 0.2 | 77.9 |
| 4 | 2:1 | 50 | 3 | 301 | trace | 0.5 | 78.0 | 0.7 | 77.5 |
| 5 | 1.75:1 | 30 | 24 | 367 | trace | 1.8 | 65.9 | trace | 79.7 |

*Determined by means of high pressure liquid chromatograhy; the % by weight to make up tp 100% comprises $H_2O$ and $H_2SO_4$.

The invention thus furthermore relates to a process for the preparation of 1-naphthylamine-2,4,6-trisulphonic acid.

The process is characterised in that the sulphonation mixture obtained in the preparation of 1-naphthylamine-4,6-disulphonic acid is reacted, in a second sulphonation stage, with oleum at temperatures from 70° to 120° C., preferably 80° to 100° C., the amount of oleum being such that 1 to 2.5 mols, preferably 1.5 to 2 mols, of sulphur trioxide are present per mol of 1-naphthylamine-6-sulphonic acid originally employed.

The oleum to be used can contain 20 to 100% by weight of sulphur trioxide. Oleum which contains 50 to 80 percent by weight of free sulphur trioxide is preferably used.

EXAMPLE 1

700 g of 100% strength sulphuric acid are initially introduced into a reaction vessel provided with a stirrer, dropping funnel, internal thermometer and drying tube. 226.8 g (1 mol) of 1-naphthylamine-6-sulphonic acid (98% pure) are introduced into this sulphuric acid at a maximum temperature of 40° C. in the course of 30 minutes while stirring. The mixture is stirred until a

EXAMPLE 6

(Sulphonation according to British Patent Specification No. 15,223)

780 g of oleum (25% strength) (2.44 mols of $SO_3$) are initially introduced into the sulphonation apparatus used in Example 1. 225 g (1 mol) of 1-naphthylamine-6-sulphonic acid (99% pure) are introduced into this oleum at 20° C. in the course of 30 minutes. The sulphonation mixture is then subsequently stirred in 50° C. for 4 hours.

The yield of 1-naphthylamine-4,6-disulphonic acid, determined by high pressure liquid chromatography of the finished sulphonation product, is 62% of theory, relative to the 1-naphthylamine-6-sulphonic acid employed.

According to high pressure liquid chromatography, the sulphonation mixture has the following composition: 1-naphthylamine-4,6-disulphonic acid: 18.7% by weight (62.0 mol %); 1-naphthylamine-3,6-disulphonic acid: 7.49% by weight (24.8 mol %); and 1-naphthylamine-2,4,6-trisulphonic acid: 3.44% by weight (9.0 mol %).

EXAMPLE 7

700 g of 100% strength sulphuric acid are initially introduced into the sulphonation apparatus used in Example 1. 225 g (1 mol) of 1-naphthylamine-6-sulphonic acid (99% pure) are introduced into this monohydrate at a maximum temperature of 40° C. 246 g of 65% strength oleum (=2 mols of SO₃) are added dropwise to this mixture at 30° C. in the course of 30 minutes. The sulphonation mixture is then stirred at 30° C. for 16 hours.

A further 246 g of 65% strength oleum (=2 mols of SO₃) are then added. The sulphonation mixture is warmed to 90° C. in the course of 6 hours, whilst stirring, and is then cooled to 20° to 30° C. and introduced into 2,600 g of water at a rate such that the temperature of the aqueous mixture formed rises to 95° C. 250 g of sodium chloride are added to the aqueous mixture, the mixture is cooled to 20° C. in the course of 5 to 6 hours and the precipitate is filtered off and washed with saturated sodium chloride solution until the runnings of this solution are almost colourless. The solid is dried at 90° C. in a vacuum drying cabinet.

The yield of the disodium salt of 1-naphthylamine-2,4,6-trisulphonic acid is 553 g=87.7% of theory, relative to 1-naphthylamine-6-sulphonic acid. ;p According to high pressure liquid chromatography, the product filtered off has the following composition: 1-naphthylamine-2,4,6-trisulphonic acid: 60.7% by weight; 1-naphthylamine-3,6-disulphonic acid: 1.15% by weight; 1-naphthylamine-4,6-disulphonic acid: 0.2% by weight; remainder to make up to 100%: $H_2O$/NaCl.

EXAMPLE 8

(Sulphonation according to British Patent Specification No. 15,223)

780 g of 25% strength oleum (=2.44 mols of SO₃) are initially introduced into the sulphonation apparatus used in Example 1. 225 g (1 mol) of 1-naphthylamine-6-sulphonic acid (99% pure) are introduced into this oleum at 20° C. in the course of 30 minutes, whilst cooling. The sulphonation mixture is then warmed to 50° C. for 4 hours. 240 g of S65% strength oleum (=1.95 mols of SO₃) are then added rapidly dropwise. The mixture warms to 90° C. in the course of 4.5 hours. The sulphonation mixture is then cooled to 20° to 30° C. and introduced into 2,600 g of water at a rate such that the temperature of the aqueous mixture rises to about 95° C. 250 g of sodium chloride are added to the aqueous mixture and the mixture is allowed to cool to 20° C. in the course of about 5 to 6 hours. The solid which has precipitated is filtered off and washed with saturated sodium chloride solution until the runnings of sodium chloride solution are almost colourless. The solid is dried at 90° C. in a vacuum drying cabinet.

The yield of the disodium salt of 1-naphthylamine-2,4,6-trisulphonic acid is 506 g (=57.5% of theory relative to 1-naphthylamine-6-sulphonic acid).

According to high pressure liquid chromatography, the product isolated has the following composition: 1-naphthylamine-2,4,6-trisulphonic acid 43.5% by weight;

1-naphthylamine-3,6-disulphonic acid 7.5% by weight; 1-naphthylamine-4,6-disulphonic acid 0.15% by weight; remainder to make up 100%: $H_2O$/NaCl

What is claimed is:

1. In the process for the preparation of 1-naphthylamine-4,6-disulphonic acid by sulphonating 1-naphthylamine-6-sulphonic acid with oleum, working up the sulphonation mixture by introducing it into water, and isolating the 1-naphthylamine-4,6-disulphonic acid, the improvement comprising
   (a) adding the oleum at a temperature of 10° to 70° C., either simultaneously with the 1-naphthylamine-6-sulphonic acid to initially introduced sulphuric acid, or to 1-naphthylamine-6-sulphonic acid, which is dissolved or suspended in sulphuric acid, and
   (b) using such a molar ratio of sulphur trioxide to 1-naphthylamine-6-sulphonic acid that 1.2 to 3 mols of sulphur trioxide are present per mol of 1-naphthylamine-6-sulphonic acid.

2. The process according to claim 1, wherein the molar ratio of sulfur trioxide to 1-naphthylamine-6-sulphonic acid is such that 1.5 to 2.5 mols of sulfur trioxide are present per mol of 1-naphthylamine-6-sulphonic aic.

3. The process according to claim 1, wherein 80 to 100% strength sulphuric acid is used as the initial component or for obtaining the solution or suspension.

4. The process according to claim 1, wherein the 80 to 100% strength sulphuric acid is used in such an amount that 6 to 8 mols of sulphuric acid are present per mol of 1-naphthylamine-6-sulphonic acid.

5. The process according to claim 1, wherein the oleum is added at a temperature of 20° to 40° C.

6. A process for the preparation of 1-naphthylamine-2,4,6-trisulphonic acid, wherein the 1-naphthylamine-4,6-disulphonic acid prepared according to the process of claim 1 is then reacted, in a second sulphonation stage, with oleum at a temperature of 70° to 120° C., the amount of oleum being such that 1 to 2.5 mols of sulphur trioxide are present per mol of 1-naphthylamine-6-sulphonic acid.

* * * * *